United States Patent [19]

Bartilson et al.

[11] Patent Number: 4,848,165
[45] Date of Patent: Jul. 18, 1989

[54] SMEAR SAMPLING APPARATUS

[75] Inventors: Benjamin M. Bartilson; Kenneth D. Kok; Thomas A. Pettenski, all of Columbus, Ohio

[73] Assignee: Battelle Memorial Institute, Columbus, Ohio

[21] Appl. No.: 136,678

[22] Filed: Dec. 22, 1987

Related U.S. Application Data

[63] Continuation-in-part of Ser. No. 931,373, Nov. 14, 1986, abandoned, which is a continuation-in-part of Ser. No. 740,148, Jun. 3, 1985, abandoned.

[51] Int. Cl.$^4$ ............................................. G01N 1/04
[52] U.S. Cl. ................................................. 73/864.71
[58] Field of Search ..................... 73/863, 863.91, 864, 73/864.41, 864.71

[56] References Cited

U.S. PATENT DOCUMENTS

| | | | |
|---|---|---|---|
| 3,066,342 | 12/1962 | Jackson et al. | 73/864.71 |
| 3,074,276 | 1/1963 | Moos | 73/864.71 |
| 3,091,967 | 6/1963 | Hurdlow et al. | 73/864.71 |
| 3,430,496 | 3/1969 | Swanberg et al. | 73/864.71 |
| 3,554,039 | 1/1971 | Braun | 73/864.71 |
| 4,103,553 | 8/1978 | DeBlasiis et al. | 73/864.71 |

Primary Examiner—Stewart J. Levy
Assistant Examiner—Robert R. Raevis
Attorney, Agent, or Firm—Klaus H. Wiesmann

[57] ABSTRACT

Apparatus for taking smear samples of the surface of objects for sampling radiation or chemical contamination levels. Both wiping area and pressure are controlled giving reliable, repeatable samples. A carriage provided with sampling strips is slideably mounted within a frame. Constant force springs pull the carriage across a known distance upon its release while a pressure roller on the carriage presses the sample strip to the area to be sampled. The sample strip is wound on a take-up reel as each sample is taken. The device is intended for remote or hazardous environments and may be operated manually or by robotics.

7 Claims, 5 Drawing Sheets

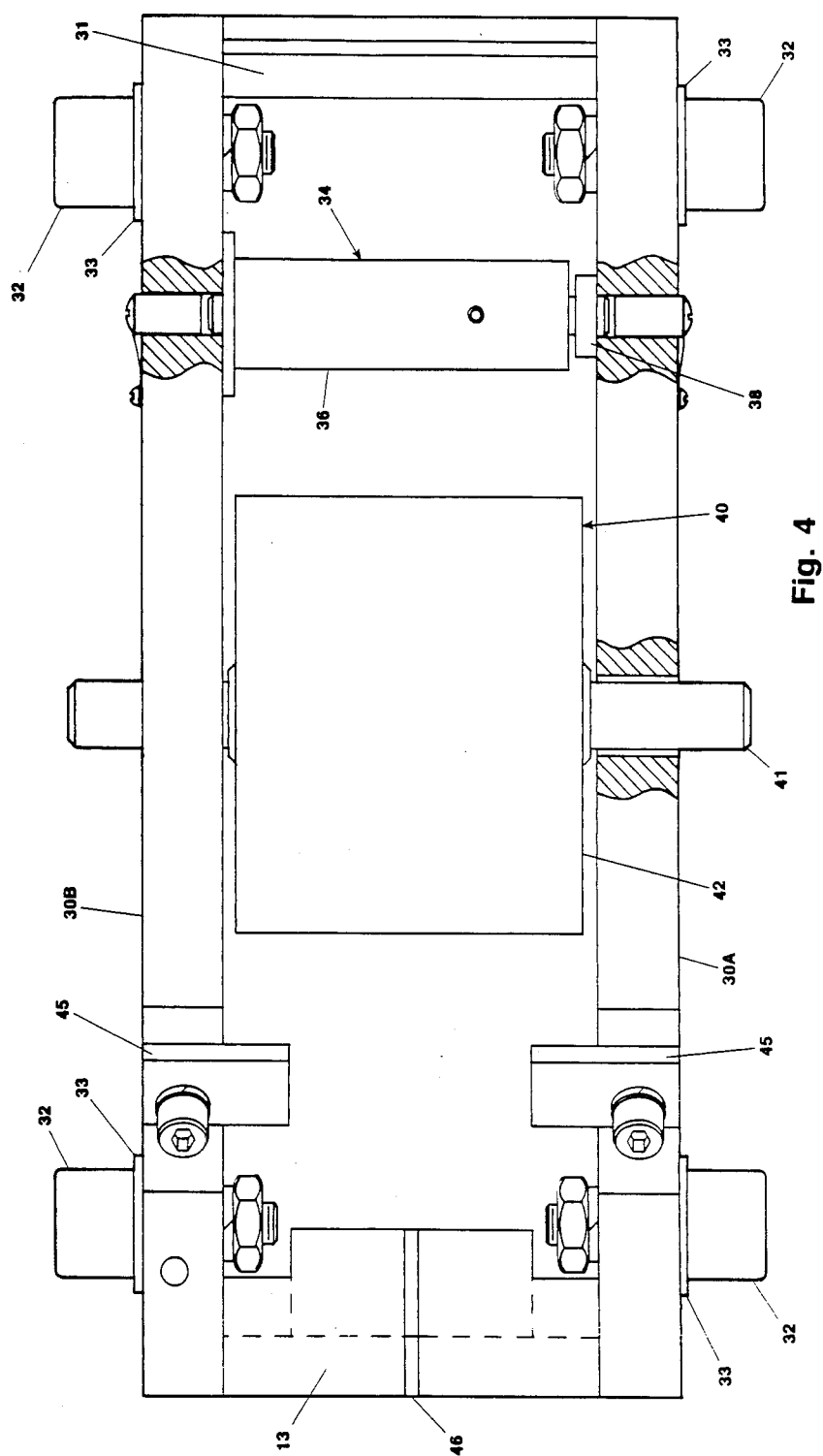

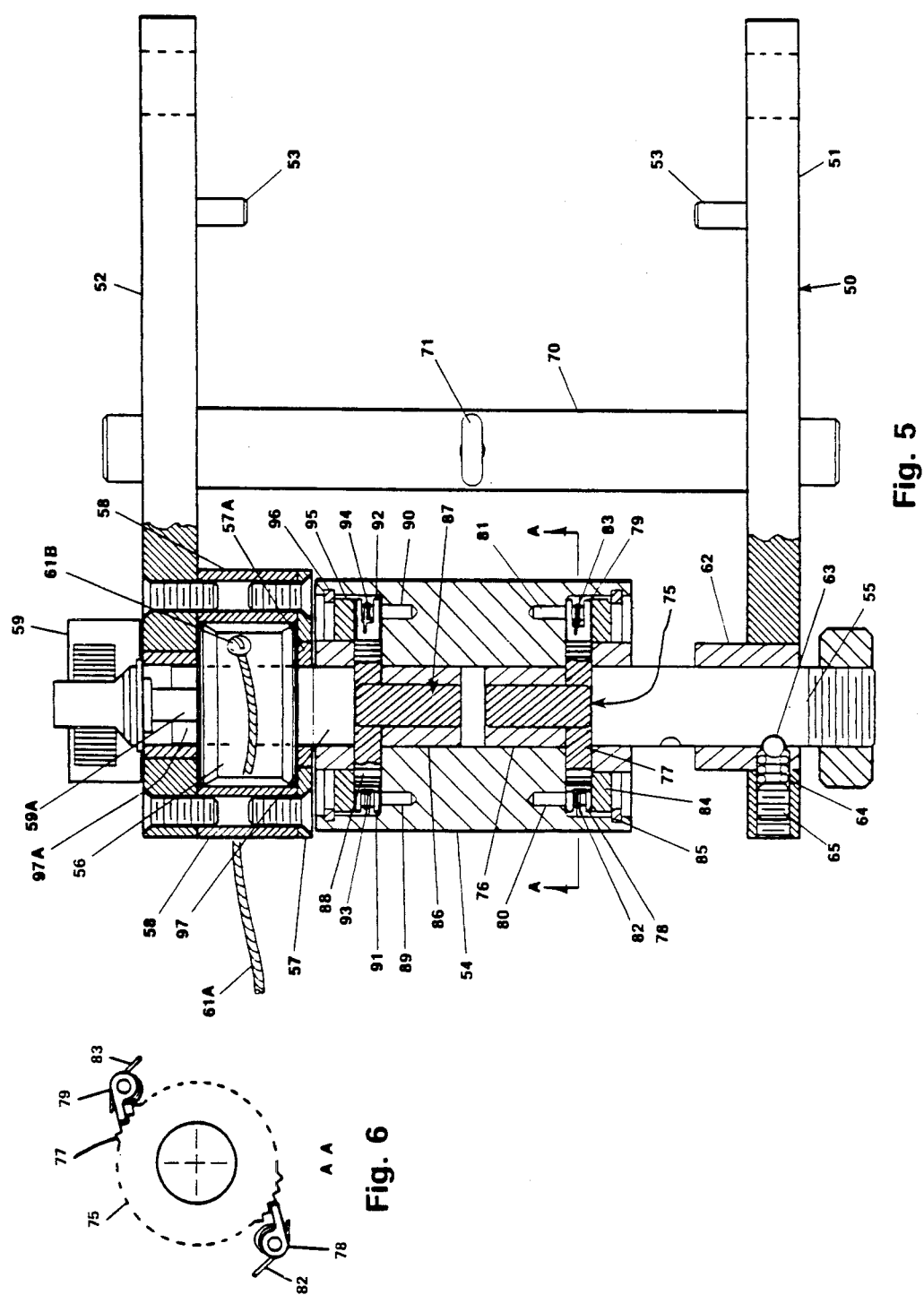

SMEAR SAMPLING APPARATUS

The present application is a continuation in part of U.S. patent application Ser. No. 931,373 filed Nov. 14, 1986; now abandoned which is a continuation-in-part of U.S. patent application Ser. No. 740,148 filed June 3, 1985, now abandoned.

FIELD OF THE INVENTION

This invention relates to a smear sampling device for sampling radiation or chemical contamination levels on the surface of objects. The device has utility in sampling surface contamination in remote sites and in hazardous environments. The device has further utility in that it may be operated on a robot arm. The device further allows reliable, repeatable sample collection.

BACKGROUND OF THE INVENTION

Smear samples are often required in the chemical or nuclear industry to monitor contamination of a given surface. Typically these samples are taken manually by health physics technicians wiping or smearing a piece of filter paper across a potentially contaminated surface so that contaminants are absorbed on the paper. It is critical that the area wiped be kept constant to allow proper measurement of contamination and also allow easy comparison with other samples. A typical area would be 100 square centimeters. After wiping, the filter paper is placed into a counter or is chemically analyzed to determine the level of radioactivity or chemical contamination that is picked up from the area sampled.

This technique suffers from several drawbacks. Both wiping pressure and area sampled can vary depending on the person conducting the test and the technique used. Thus, consistency from sample to sample is a problem. In addition, the person conducting the smear tests is risking exposure to radiation and possibly dangerous environments.

It is an object of the present invention to overcome the various shortcomings of the previous sampling methods by providing an apparatus that can give reliable, repeatable samples by a constant wiping pressure and smear area. It is a further object of the invention to provide an apparatus that can be used manually or remotely to sample the degree of surface contamination whether by radioactive or chemical materials.

BRIEF DESCRIPTION OF THE INVENTION

The apparatus of the invention is a smear sampling device that can be used manually or remotely to determine the degree of radioactive or chemical surface contamination. The apparatus takes consistent samples by using a constant wiping pressure and smear area. In the preferred embodiment the apparatus consists of a frame having two rails which guide a carriage driven by a constant force spring or other driving means. Carriage movement is activated by spring loaded pins which release the carriage when the apparatus is pushed firmly on a test surface. As the carriage is pulled by the driving means, a pressure roller on the carriage pushes the sampling paper on the test surface performing the smear. The take-up reel for the filter paper is located on an arm that is mounted on the carriage. When the carriage is reset the take-up reel automatically winds up the previous smear sample and is ready to take another smear. Identification marks may be added to each sample for later identification.

BRIEF DESCRIPTION OF THE DRAWINGS

FIG. 4 illustrates details of the carriage with cutaway portions.

FIG. 5 illustrates details of the arm assembly 50 and take-up roller with cutaway portions.

FIG. 6 illustrates details of the ratchet bushing and pawls.

DETAILED DESCRIPTION OF THE INVENTION

Figure 1:
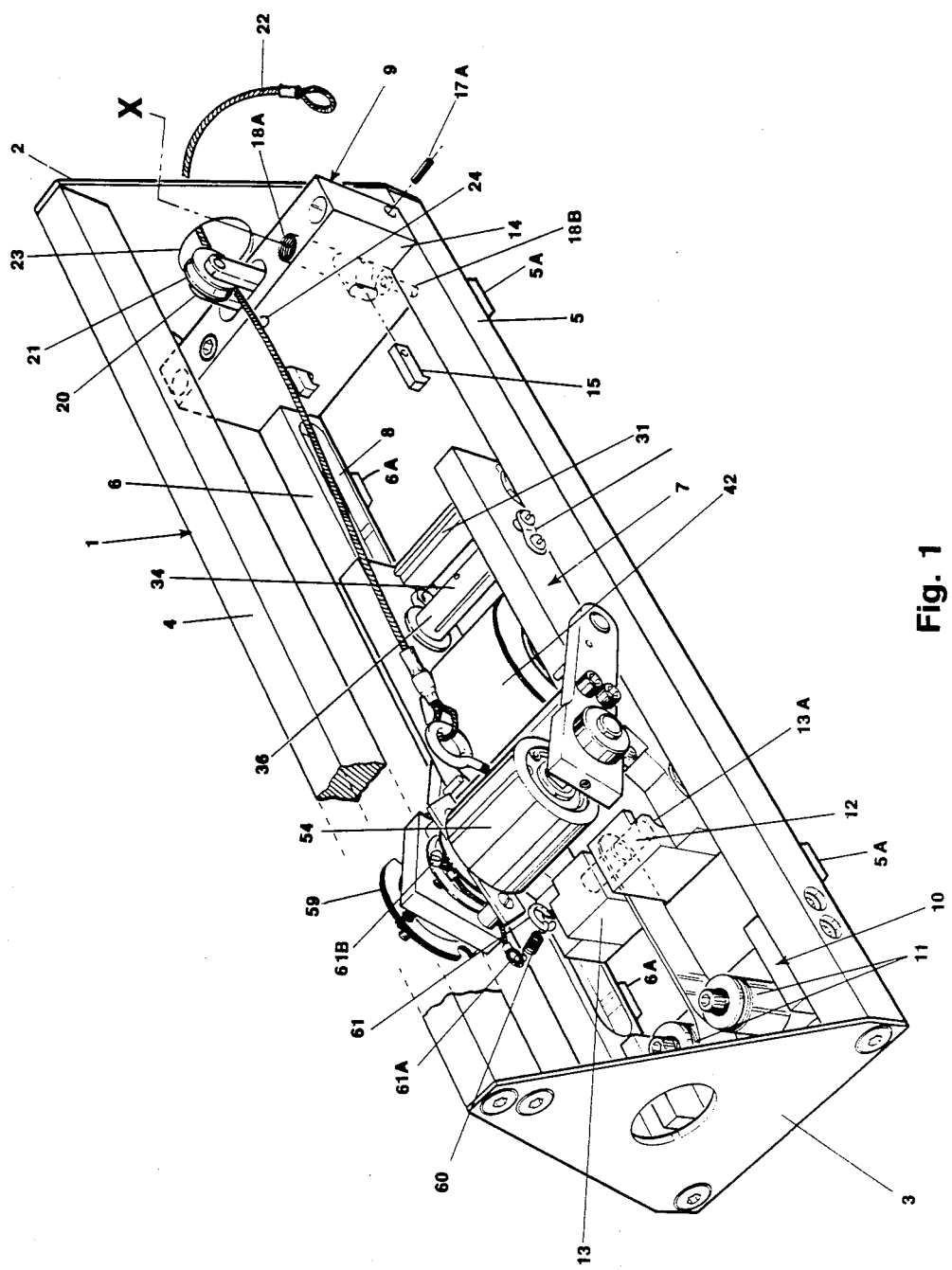
FIG. 1 illustrates an isometric view of one embodiment of the invention.
Figure 2:
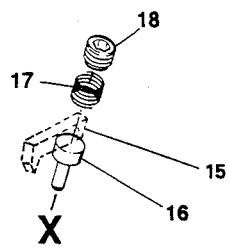
FIG. 2 illustrates details of the pressure sensing and release mechanism that inserts at X in FIG. 1.

In FIG. 1 the apparatus of the invention is shown in an intermediate position to better illustrate the mechanism and function thereof. A frame 1 comprises end pieces 2,3 joined by an upper support bar 4 and two lower side rails 5,6. Within the frame a carriage 7 slides back and forth in grooves 8 disposed in each side rail 5,6. At one end of the frame 1 is mounted a release means or release mechanism 9 and at the opposing end is mounted a constant force spring motor assembly 10. The carriage 7 slides between these two extremes being held by the release mechanism 9 and sliding to the opposing end by action of power means or Negator® springs 11 mounted on the spring motor assembly 10. The Negator® spring may also be referred to as a constant force spring. A rubber cushioning strip (not shown) may be provided at spring motor assembly 10 to cushion the shock produced when the carriage 7 reaches the end of its travel at the spring motor assembly 10. A motor spring end connector 12 shown in dashed lines connects both springs 11 as a unit to the carriage 7 by the motor spring connector mount 13 having a radial groove 13A within which the connector 12 may be mounted. The pressure sensing and release mechanism 9 consists of a release block 14 having mounted therein two release links 15 that hold the carriage 7 in place prior to sampling. FIG. 2 illustrates further details of the pressure sensing and release mechanism 9 where two release pins 16 are used to trigger the release links 15. The release pins 16 are spring loaded by spring 17 and can be adjusted to respond to any desired actuating pressure by a threaded biasing plu 18. Pins 17a rotably hold the release links 15. All of the parts shown in FIG. 2 are inserted within threaded hole 18A. Release pins 16 are of sufficient length to project through hole 18B and out beyond the bottom of release mechanism 9.

Also mounted on the pressure sensing and release mechanism 9 is a pulley mount 20 having a pulley 21 that is used to guide a reset cable 22. Reset cable 22 exits the device through a hole 23 in the end piece 2. The pulley mount 20 is attached to release block 14 by a pin 24 that allows the mount 20 freedom to rotate about the pin 24.

The carriage 7 is further illustrated in FIG. 4. The carriage 7 consists of two side plates 30A, 30B joined at one end by a catch release block 31 and motor spring connector block 13. Catch release links 15 hold the carriage 7 by engaging with the catch release block 31.

Further details of carriage 7 include four cam follower assemblies 32 that slide in grooves 8 in the side rails 5,6. A shim 33 separates the side plates 30A, 30B from the side rails 5,6 to prevent skewed carriage motion by taking out side play between the carriage 7 and rails 5,6.

Figure 3:
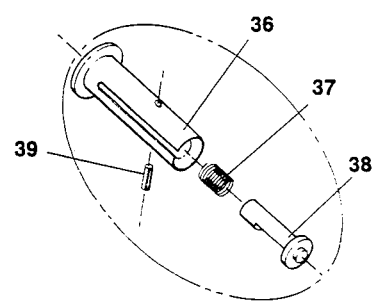
FIG. 3 illustrates details of the feed reel 34.

A feed reel 34 shown in FIGS. 3 and 4 is easily removable with the aid of removal pins 35 and springs 35A. The reel 34 consists of a reel body 36, a spring 37 and retainer 38. A pin 39 passes into the feed reel 34 sufficiently to catch retainer 38 and prevent it from coming completely out of the reel 34.

A pressure roller assembly 40 is mounted adjacent to the feed reel 34. The pressure roller assembly 40 consists of a shaft 41 having a resilient roller 42 pressed thereon. The outer diameter of pressure roller 42 projects some distance below the surface of the siderail 5,6 that contact the surface to be sampled. The exact amount of projection needed depends on the compliancy of the roller, the degree of compression desired on the roller and the footprint characteristics desired. A preferred amount is about 6 mm. Pads 5A and 6A control the contact of the apparatus with the surface. Various thicknesses of pads 5A,6A can be used to adjust contact of the roller 42 and minimize contact of the apparatus with the surface to be sampled. The roller 42 has a bearing (not shown) to provide low friction as it turns on the shaft 41. Compliancy of roller 42 should be selected to provide a sufficiently broad footprint for the sample paper. This will allow enough active area on the sample strip to collect contaminants. In the present embodiment a sponge rubber material is used for pressure roller 42. Marker means 45 are mounted on the carriage 7 to mark each sample. The marker means 45 may be knife edges that cut a small mark, pens or a stamp that sequentially numbers each sample. At the end of the carriage 7 is mounted a motor spring block 13 that has a slot 46 for the constant force springs 11 and a radial groove 13A within which is mounted the motor spring connector 12.

Also mounted on the carriage 7 is an arm assembly 50 comprising a first arm 51 and a second arm 52. These arms 51,52 are rotably mounted to a portion of the pressure roller shaft 41 that extends through the carriage side plates 30A, 30B. Pins 53 prevent rotation of the arms 51,52 beyond a set limit in either direction. Connected between the arms is a take-up reel 54. The reel 54 is connected to the arm 51 through a square pin 55 and to a pulley 56 by a second square shaft 97. Support for the pulley 56 is by a retainer plate 57 with a bushing 57A and standoffs 58 that are mounted to arm 52. The pulley 56 in turn is connected to a second constant force spring motor 59 by an allen key 59A. The spring motor 59 is mounted to the opposing surface of arm 52 and is adapted to provide power to the pulley 56 and take-up spool 54. A spring 60 mounted to the carriage 7 by a connector 61 at the negator (trademark) spring connector 13 provides an opposing force to the constant force spring motor 59. The spring 60, is connected to the pulley 56 by wire 61A and screw 61B. In FIG. 1, the spring 60 and wire 61A are shown in an untensioned position. This would not normally be the case, they are shown this way for purposes of illustration only, normally the wire 61A and spring 60 are taut and pull the arm assembly 50 down. A cross arm 70 connects arms 51,52. This cross arm 70 is connected to the wire cable 22 by connector 71.

Further details of the take-up reel 54 and arm 50 are shown in FIGS. 5 and 6. Square pin 55 is retained by a square bushing 62 and a ball 63, spring 64 and screw 65 that prevent movement of the pin 55 in normal operation. The ball retention allows easy removal of the take-up reel 54 to retrieve sample materials wound thereon. The square pin 55 fits into a square mating portion of a ratchet assembly 75 that is rotably mounted in the take-up reel 54 by fitting into bushing 76. The circumference of the ratchet assembly 75 has a series of teeth 77 that engage a set of pawls 78,79 and prevent rotation of the take-up reel 54 except in the clockwise direction. The clockwise direction is that resulting in winding of sample strips on the take-up reel 54. The clockwise direction is referenced by viewing the take-up reel 54 from arm 51. Both pawls 78,79 prevent rotation in the same direction but are offset from one another by 5 degrees to provide finer resolution. The pawls are mounted on pins 80,81 and are biased by torsion springs 82,83. The pawls 78,79 and ratchet assembly 75 are held in place by the retainer spacer 84 and snap ring 85.

The opposing end of the take-up reel 54 has a similar arrangement of bushing 86, second ratchet assembly 87, teeth 88, pins 89,90, pawls 91,92, springs 93,94, retainer spacer 95 and snap ring 96. On this end the teeth 88 and pawls 91,92 are again arranged to allow rotation of the take-up roller 54 in a clockwise direction when viewed from the carriage arm 51. The second ratchet assembly 87 is fitted over a square shaft 97 that is rounded where it passes through the retainer plate 57 then connects to the pulley 56. The pulley is rotably mounted to the second side arm 52 by shaft 97A that allows free rotation of the pulley 52 with respect to the side arm 52. The pulley 56 connects to the constant force spring motor 59 by an allen key 59A that fits within the pulley shaft 97A and acts to energize the motor each time the apparatus takes a new sample.

Sampling strip or paper 700 is mounted on feed reel 34 by winding in a clockwise or counterclockwise direction as desired when viewed from side piece 30A. Alternate paper paths are shown as 701 and 702 respectively as in FIG. 7. The sampling paper passes between the pressure roller 42 and the surface to be sampled, then over the take-up reel 54 in a clockwise direction and the end fastened to the take-up reel 54 by tape or other appropriate means. The screw 61B acts to limit the motion of the pulley and thus the motor 59 and take-up reel 54 by engaging the standoffs 58.

Operation of the apparatus is further described below. The apparatus is carried to the appropriate area to be sampled either manually or by a robotic or manipulative device. The apparatus is prepared for operation by pulling the reset cable 22 sufficiently to cause the carriage 7 to travel toward the release mechanism 9 and engage release links 15 with the catch release block 31. This action energizes springs 11 and places the carriage 7 in tension. Simultaneously with the reset action on the carriage 7 the arm assembly 50 is pivoted forward toward the release mechanism end of the apparatus. This action pulls fresh sample paper from the feed spool 34 by lengthening the sample path distance between the take-up roller 54 and feed spool 34. At the same time the pulley 56 is rotated counterclockwise (viewed from arm 51) by the action of spring 60. This relative movement is allowed by the ratchet assembly 87 and pawls 91,92 because the action is the same as if the take-up reel 54 had turned clockwise. The take-up reel 54, however, cannot move counterclockwise relative to ratchet assembly 75 and thus remains stationary on the arm assembly 50. The counterclockwise rotation of the pulley 56 energizes the spring motor 59 and prepares it for driving the take-up reel 54 when the reset cable 22 is released. The spring motor 59 is energized to the extent that the pulley 56 rotates. The pulley's rotation in the present embodiment is limited by the travel permitted by the screw 61B which projects sufficiently to be limited by standoffs 58; however, other travel limits could be chosen as needed by other appropriate stops.

Upon release of the reset cable 22 the carriage 7 is held in place by release links 15. The arm assembly, however, swings backward, impelled by the action of spring 60 until the pins 53 engage the carriage side pieces 30A,30B. As the arm assembly moves backward the take-up reel 54 is rotated by the constant force spring motor 59 to take-up the slack now appearing in the sampling paper. The pulley 56 and spring motor 59 then rotate together with take-up reel 54. The spring motor 59 remains partially energized at the end of each reset operation biasing the take-up reel 54 forward until the screw 61B hits the standoffs 58.

Details of the operation of the marking means are as follows. At each reset operation the movement of the arm assembly 50 can be used to mark each sample by a knife notch, pen mark or stamp mark. The knife notch and pen mark or stamp can be used to mark the beginning and end of each strip containing sample. A stamp mark can be used to number the samples so that each can be positively identified. A means that indexes and stamps each sample is preferred. This can easily be installed by those skilled in the art.

FIG. 4 illustrates one embodiment of the invention using knife edges to notch the paper. The paper passes between roller 42 and marking means 45. When the arm assembly 50 swings back to the reset position it pushes the paper against the marker means 45 thus notching the paper. If the marker means are pens or a stamp the appropriate impression would be placed on the paper. If a stamp is used a serial marking system can be used where the individual samples are individually numbered. The pressure of the paper against the marking means being used to index the numbers in the stamp in a manner well-known in the art.

Figure 7:
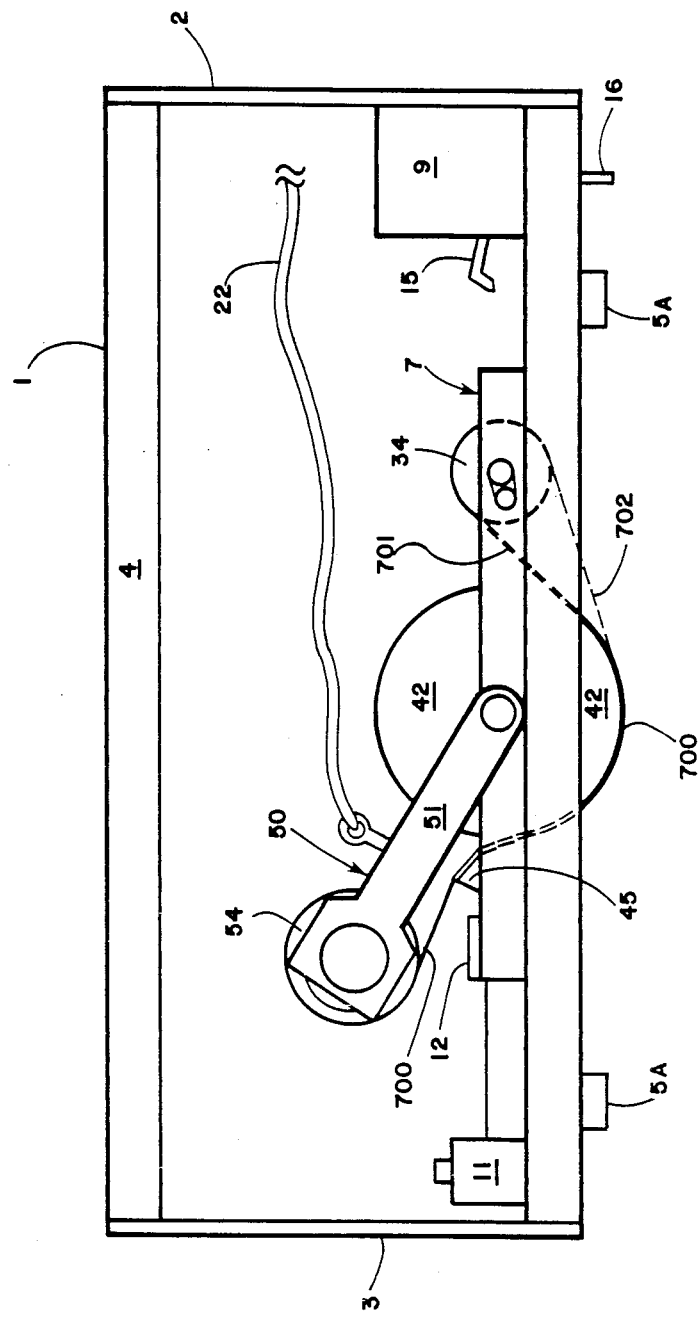
FIG. 7 illustrates one embodiment illustrating further details of the sample paper path and marking means.

Marking means 45 is contacted every time a new sample is advanced. This action results from the reset operation where arm assembly 51 is pulled toward end 2 of the apparatus. When the reset cable 22 is released arm assembly 51 is pulled toward end 3 by spring 60. As the arm rotates toward end 3 the paper 700 contacts marking means 45. This action is best seen in FIG. 7 that shows a side view of one embodiment of the invention. Paper travel is to left from spool assembly 34 under roller 42 over marking means 45 to spool 54.

Once the apparatus is reset and ready for operation it is placed on a surface to be sampled. Sufficient force is then applied to the apparatus to press the pads 5A,6A of the apparatus against the surface to be sampled and depress pins 16. When the force is sufficient to overcome the force of springs 17 the pins 16 move upward into release mechanism 9 and release links 15. The release links 15 rotate about pins 17A as pin 16 moves upward rotating links 15 and thus releasing the carriage 7. A certain pressure on roller 42 is required to obtain a desired footprint that is related to roller compliancy and amount of roller projection. A softer roller provides a larger area for a given pressure. Once a roller has been selected and its desired degree of compression determined the pressure required for the desired footprint and frictional characteristics for wiping a surface can also be readily determined. The pressure at which the apparatus responds can be preset by appropriate selection of springs 17 and spring bias setting with biasing plug 18, and thickness of pads 5A,6A. When sufficient force is applied on the apparatus and the appropriate preset pressure level is reached the pins will depress and release carriage 7. Thus the pins 16 in effect are responding when the appropriate pressure level required for proper wiping with the sample strip is present. This results in repeatable and reliable pressures for all samples.

As carriage 7 is released it moves toward the other end of the apparatus by the action of springs 11 or other means. Constant force (Negator ®) springs are preferred in that they are lightweight, reliable and give constant forces over the length of travel of the carriage 7. As carriage 7 moves, the pressure roller 42 presses the sampling strip or paper under roller 42 in engagement with an area of the surface to be sampled. The sample strip is thus wiped across a known area determined by sample strip width and length of carriage travel. The sample strip is firmly held by take-up reel 54 because the force on the sample strip acts in the direction that the take-up spool 54 is prevented from rotating by the action of pawls 78,79.

Sample collection with the apparatus of the invention is as follows. The apparatus 1 is moved toward a surface to be measured. As the pads 5A,6A touch the surface release pins 16 are simultaneously depressed so that the carriage 7 released and the surface wiped with a given area of paper 700. The springs 17 provide the resistance for pins 16 that determines the pressure required to push the pins and release the carriage 7. Resilient roller 42 extends a preset distance beyond the surface of the plane defined by pads 5A,6A. Thus, resilient roller 42 is compressed in a consistent repeatable manner as the apparatus is pressed on a surface to be sampled when all pads 5A,6A touch that surface. Repeatable and reliable measurements may be made by pressing the apparatus on a surface so that all pads 5A,6A are in contact with the surface as the release pins 16 rotate the links 15 that hold the carriage 7.

The invention may also be generally described as a smear sampling apparatus having a frame 1 with pads 5A,6A mounted thereon adapted for contacting a surface to be sampled; a carriage 7 slideably disposed within the frame 1; a carriage 7 driving means mounted between the frame 1 and carriage 7 to move the carriage 7 relative to the frame 1; sampling means mounted to the carriage 7 and adapted to feed a sample paper strip 700 from a feed spool, position the paper on a pressure roller 42 and store a plurality of samples on a take-up reel 54, where the sampling means is disposed on the carriage 7 so that the sample paper is contacted and moved across a surface as the carriage 7 moves within the frame; a pressure sensing and release means 9 mounted at one end of the frame 1, adapted to hold the carriage 7 until a condition, a selected pressure, at a point of contact of the sampling means and surface to be sampled is sensed whereon the carriage 7 is released to move within frame 1 and wipe the surface with the sample paper; and reset means operably mounted to the carriage 7 and sampling means and adapted to reset the release, driving and sampling means as each sample is taken so as to provide for a plurality of samples. The pressure sensing and release means, driving means, sampling means and reset means can be mechanically (spring), pneumatically or electrically powered or a combination of any of the above power means.

The pressure sensing and release means may include a release block 14 and a plurality of release pins 16, release links 15 and springs 17 disposed in the block 14 and operatively interconnected to hold the carriage 7 until the release pins 16 are depressed. The release means may also include a plurality of electrical pressure sensors known in the art in place of the pins and operatively connected to a plurality of release links to release the carriage 7 upon sensing a predetermined pressure.

The carriage driving means may include a spring mounted between the frame and carriage; a constant force spring 11 mounted between the frame and carriage; a pneumatic cylinder mounted between the frame and carriage; or an electrical motor mounted between the frame and carriage. The sampling means consists of a feed spool 34 rotably mounted on the carriage 7; a pressure roller 42 rotably mounted on the carriage 7; a take-up reel 54 rotably mounted to the reset means; and wherein the feed spool 34, pressure roller 42, and take-up reel 54 are adapted to operate with a sampling strip 700 disposed on the feed roller 34, and passing between the pressure roller 42 and a surface to be sampled, and finally winding on the take-up reel 54.

The reset means can generally be described as a side arm assembly 50 having first and second side arms 51,52 adapted to rotate when pulled by a reset force so as to pull fresh sample strip from the feed reel 34 by lengthening the sample paper path distance between the take-up reel 54 and feed spool 34; a first ratchet means operatively mounted to the take-up reel and one side arm 51 so as to allow rotation in only one direction and prevent unwinding of the take-up reel 54; a second ratchet means operatively mounted to the take-up reel 54 so as to allow rotation of the take-up reel 54 only in the same direction as the first ratchet means; a pulley 56 with a first shaft 97 operatively mounted to the second ratchet means and a second shaft rotably mounted to the second side arm 52, a constant force spring motor 59 mounted to the second side arm 52 with the motor shaft connected to the second pulley shaft and adapted to drive the pulley 56 and take-up reel 54 through the second ratchet means to wind the samples thereon; a spring 60 attached between the pulley 56 and carriage 7 adapted to rotate the pulley 56 and constant force spring motor 59 when the apparatus is reset so as to recharge the constant force spring motor 59; and a reset cable 22 attached to the side arm assembly 50 that provides the pulling force for the reset operation. The first ratchet means includes square pins 55, ratchet assembly 75, pins 80,81, pawls 78,79, torsion springs 82,83, plate 84 and snap ring 85. The second ratchet means includes equivalent parts on the other portions of the take-up reel 54.

Another embodiment of the reset means can further include a cable disposed on the carriage and adapted to pull the carriage to its initial position; and an electrical stepping motor operatively mounted to the carriage 7 and take-up reel 54 that is adapted to rotate the take-up reel 54 so as to wind a sample strip thereon. The cable can be replaced by an electric motor disposed between the frame and carriage 7 and adapted to pull the carriage 7 to its initial position. A final embodiment of the reset means includes a pneumatic cylinder disposed between the carriage and frame; a pneumatic motor operatively mounted to the carriage 7 and take-up reel 54 that is adapted to rotate the take-up reel 54 so as to wind a sample strip thereon.

While the forms of the invention herein disclosed constitute presently preferred embodiments, many others are possible. It is not intended herein to mention all of the possible equivalent forms or ramifications of the invention. It is to be understood that the terms used herein are merely descriptive rather than limiting, and that various changes may be made without departing from the spirit or scope of the invention.

We claim:

1. A smear sampling apparatus comprising:
   a. a frame with pads mounted thereon adapted for contacting a surface to be sampled;
   b. a carriage slideably disposed within the frame;
   c. carriage driving means mounted between the frame and carriage to move the carriage;
   d. sampling means mounted to the carriage adapted to feed a sample paper strip from a feed spool, position the paper on a pressure roller, and store a plurality of samples on a take-up reel, where the sampling means is disposed on the carriage so that the sample paper is contacted and moved across a surface as the carriage moves within the frame;
   e. a pressure sensing and release means mounted at one end of the frame adapted to hold the carriage until a condition, a selected pressure, at a point of contact of the sampling means and the surface to be sampled is sensed whereon the carriage is released to move within the frame and wipe the surface with the sample paper; and
   f. reset means operably mounted to the carriage and sampling means and adapted to reset the pressure sensing and release, driving, and sampling means as each sample is taken so as to provide for a plurality of samples.

2. The apparatus of claim 1 wherein the pressure sensing and release means further comprises:
   a. a release block; and
   b. a plurality of release pins, release links and springs disposed in the block and operatively interconnected to hold the carriage until the release pins are depressed, whereby the force required to depress the release pins sufficiently to release the carriage is related to the selected pressure desired at the point of contact of the sampling means and the surface to be sampled.

3. The apparatus of claim 1 wherein the pressure sensing and release means further comprises a plurality of pressure sensors operatively connected to a plurality of release links to release the carriage upon sensing a selected pressure.

4. The apparatus of claim 1 wherein the driving means comprises a spring mounted between the frame and carriage.

5. The apparatus of claim 1 wherein the driving means comprises a constant force spring mounted between the frame and carriage.

6. The apparatus of claim 1 wherein the reset means comprises:
   a. a side arm assembly having first and second side arms adapted to rotate when pulled by a reset force so as to pull fresh sample strip from the a feed spool by lengthening the sample paper path distance between the take-up reel and feed spool;
   b. a first ratchet means operatively mounted to the take-up reel and the first side arm so as to allow rotation in only one direction and prevent unwinding of the take-up reel;
   c. a second ratchet means operatively mounted to the take-up reel so as to allow rotation of the take-up reel only in the same direction as the first ratchet means;
d. a pulley with a first shaft operatively mounted to the second ratchet means and a second shaft rotably mounted to the second side arm;
e. a constant force spring motor mounted to the second side arm with a motor shaft connected to the second pulley shaft and adapted to drive the pulley and take-up reel through the second ratchet means to wind the samples thereon;
f. a spring attached between the pulley and carriage adapted to rotate the pulley and the constant force spring motor when the apparatus is reset so as to recharge the constant force spring motor; and
g. a reset cable attached to the side arm assembly that transmits a reset force for the reset operation.

7. The apparatus of claim 1 further comprising a marking means mounted to the carriage and adapted to mark the sample paper each time the apparatus is reset.

* * * * *